US008632436B2

(12) United States Patent
Li et al.

(10) Patent No.: US 8,632,436 B2
(45) Date of Patent: Jan. 21, 2014

(54) MOTOR ASSEMBLY FOR MEDICAL EQUIPMENT

(75) Inventors: Wai To Li, Hong Kong (CN); Yue Fu Zhu, Shenzhen (CN)

(73) Assignee: Johnson Electric S.A., Murten (CH)

( * ) Notice: Subject to any disclaimer, the term of this patent is extended or adjusted under 35 U.S.C. 154(b) by 423 days.

(21) Appl. No.: 13/023,116

(22) Filed: Feb. 8, 2011

(65) Prior Publication Data

US 2011/0196375 A1 Aug. 11, 2011

(30) Foreign Application Priority Data

Feb. 9, 2010 (CN) .......................... 2010 1 0112404

(51) Int. Cl.
*F16H 3/44* (2006.01)

(52) U.S. Cl.
USPC .......................................................... 475/299

(58) Field of Classification Search
USPC .......................................................... 475/299
See application file for complete search history.

(56) References Cited

U.S. PATENT DOCUMENTS

| | | | | |
|---|---|---|---|---|
| 4,791,833 | A * | 12/1988 | Sakai et al. ................... | 475/299 |
| 5,277,527 | A * | 1/1994 | Yokota et al. ................. | 408/139 |
| 5,339,908 | A * | 8/1994 | Yokota et al. ................. | 173/216 |
| 5,451,127 | A | 9/1995 | Chung | |
| 6,086,502 | A | 7/2000 | Chung | |
| 6,142,242 | A * | 11/2000 | Okumura et al. ............... | 173/48 |
| 6,729,414 | B2 | 5/2004 | Cooper et al. | |
| 6,745,883 | B2 * | 6/2004 | Eto et al. ..................... | 192/56.62 |
| 6,892,827 | B2 * | 5/2005 | Toyama et al. ................. | 173/48 |
| 6,926,095 | B2 * | 8/2005 | Chen ................... | 173/48 |
| 6,984,188 | B2 * | 1/2006 | Potter et al. ................... | 475/298 |
| 7,407,460 | B2 * | 8/2008 | Eisenhardt ..................... | 475/303 |
| 7,882,900 | B2 * | 2/2011 | Borinato et al. .............. | 173/176 |
| 7,900,715 | B2 * | 3/2011 | Chen ........................... | 173/183 |
| 7,980,324 | B2 * | 7/2011 | Bixler et al. ................. | 173/176 |
| 8,235,137 | B2 * | 8/2012 | Walker et al. .................. | 173/47 |
| 2004/0211576 | A1 * | 10/2004 | Milbourne et al. ............. | 173/48 |
| 2009/0101376 | A1 | 4/2009 | Walker et al. | |

FOREIGN PATENT DOCUMENTS

| | | |
|---|---|---|
| CN | 201166097 Y | 12/2008 |
| GB | 2396390 A | 6/2004 |
| JP | 61090812 A | 5/1986 |
| JP | 61288909 | 12/1986 |

(Continued)

*Primary Examiner* — Dirk Wright
(74) *Attorney, Agent, or Firm* — Muncy, Geissler, Olds & Lowe, PLLC

(57) ABSTRACT

A motor assembly for use in a surgical tool, has a motor and a gear train. The gear train has an output shaft, a fixed ring gear, a movable ring gear, a cover, and a multi-stage planetary gear set. Each gear stage has a sun gear, a carrier, and planet gears mounted on one side of the carrier. The planet gears are in mesh with a sun gear and either the fixed ring gear or the movable ring gear. The movable ring gear has inner teeth formed on an inner peripheral surface and one of the carriers has outer teeth formed on an outer peripheral surface. The movable ring gear is movable between a first position where the movable ring gear is engaged with and non-rotatable relative to the cover and is disengaged from said one carrier, giving the gear train a higher gear reduction ratio, and a second position where the movable ring gear is disengaged from the cover and is engaged with and rotatable with said one carrier and the planet gears adjacent to the other side of said one carrier giving the gear train a lower gear reduction ratio.

20 Claims, 2 Drawing Sheets

(56) References Cited

FOREIGN PATENT DOCUMENTS

| | | |
|---|---|---|
| JP | 3136710 A | 6/1991 |
| JP | 6008151 A | 1/1994 |
| JP | 7145853 A | 6/1995 |
| JP | 2009072903 A | 4/2009 |
| JP | 2009125910 A | 6/2009 |

* cited by examiner

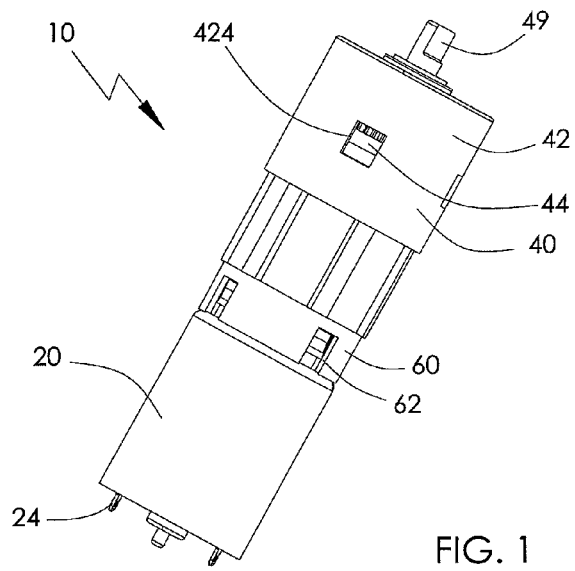
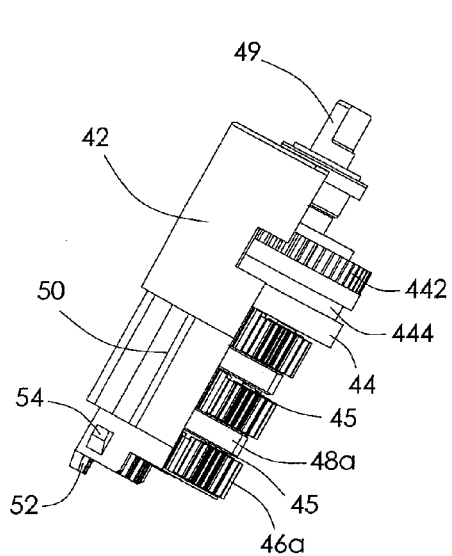
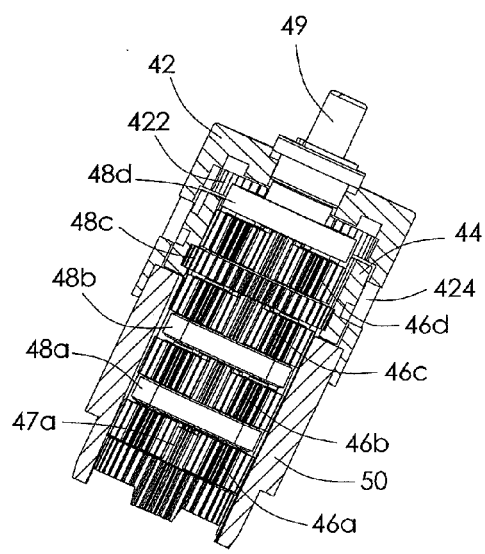
FIG. 1
FIG. 2
FIG. 3

US 8,632,436 B2

MOTOR ASSEMBLY FOR MEDICAL EQUIPMENT

CROSS REFERENCE TO RELATED APPLICATIONS

This non-provisional patent application claims priority under 35 U.S.C. §119(a) from Patent Application No. 201010112404.1 filed in The People's Republic of China on Feb. 9, 2010.

FIELD OF THE INVENTION

This invention relates to a motor assembly for medical equipment and in particular, to a surgical tool using a motor assembly having a two speed, multi-stage, planetary gear train.

BACKGROUND OF THE INVENTION

Traditional surgical tools such as surgical drills use a simple spur type gearbox. In order to operate at different speeds and torque, a special speed control circuit is used to switch the battery output voltage. However, the electric switching means used in the speed controller does not respond quickly and the controller generally is complicated and not reliable. Moreover, the control system will generate EMI which may affect other electronic medical equipment.

SUMMARY OF THE INVENTION

Hence there is a desire for a surgical tool using a motor assembly with an improved gear train which can provide different output speeds without complex electronic controls.

Accordingly, in one aspect thereof, the present invention provides a motor assembly for use in surgical equipment, comprising a motor having a motor shaft and a gear train driven by the motor, the gear train comprising: an output shaft; a fixed ring gear; a cover; a movable ring gear installed inside the cover; and a multi-stage planetary gear set, each stage comprising a sun gear, a carrier, and planet gears mounted on one side of the carrier and in mesh with the sun gear and one of the fixed ring gear and the movable ring gear, wherein the movable ring gear has inner teeth formed on an inner peripheral surface and one of the carriers has outer teeth formed on an outer peripheral surface; and the movable ring gear is movable between a first position where the movable ring gear is engaged with and non-rotatable relative to the cover and is disengaged from said one carrier, whereby the gear train has a higher gear reduction ratio, and a second position where the movable ring gear is disengaged from the cover and is engaged with and rotatable with said one carrier and the planet gears adjacent to the other side of said one carrier whereby the gear train has a lower gear reduction ratio.

Preferably, the cover has a cylindrical configuration and has inner teeth on an inner surface thereof, and the movable ring gear has outer teeth configured to engage with the inner teeth of the cover when the movable ring gear is in the first position.

Preferably, the movable ring gear has a groove in an outer surface thereof, and the cover has a through opening to provide external access to the groove for moving the movable ring gear between the first and second positions.

Preferably, the gear train comprises a four-stage planetary gear set.

Preferably, the fixed ring gear is disposed nearer to the motor than the movable ring gear and the planet gears nearer to the motor than said one carrier are in mesh with the fixed ring gear.

Preferably, when the movable ring gear is located in the first position, the planet gears adjacent to said one carrier are in mesh with the inner teeth of the movable ring gear and are rotatable relative to the movable ring gear.

Preferably, the motor is a permanent magnet direct current motor.

Preferably, the gear train includes a mounting bracket which is fixed to the motor and the fixed ring gear is fixed to the mounting bracket by a snap fit connection.

Preferably, the fixed ring gear has axially extending fingers which engage with the mounting bracket to prevent the fixed ring gear rotating with respect to the motor.

Preferably, the fixed ring gear is a connected to the cover by a tongue and groove press fit.

Preferably, the fixed ring gear, movable ring gear, cover, and planet gears are made from plastics material.

Preferably, the gear train is oil and grease free.

According to a second aspect, the present invention provides a surgical tool, switchable between drilling and screwing functions, incorporating a motor assembly as described above.

BRIEF DESCRIPTION OF THE DRAWINGS

A preferred embodiment of the invention will now be described, by way of example only, with reference to figures of the accompanying drawings. In the figures, identical structures, elements or parts that appear in more than one figure are generally labeled with a same reference numeral in all the figures in which they appear. Dimensions of components and features shown in the figures are generally chosen for convenience and clarity of presentation and are not necessarily shown to scale. The figures are listed below.

FIG. 1 is a perspective view of a motor assembly in accordance with the preferred embodiment of the present invention;

FIG. 2 is a partially sectioned view of a gear train of the motor assembly of FIG. 1;

FIG. 3 illustrates the gear train of FIG. 2 viewed from a different angle; and

DETAILED DESCRIPTION OF THE PREFERRED EMBODIMENTS

Figure 4:
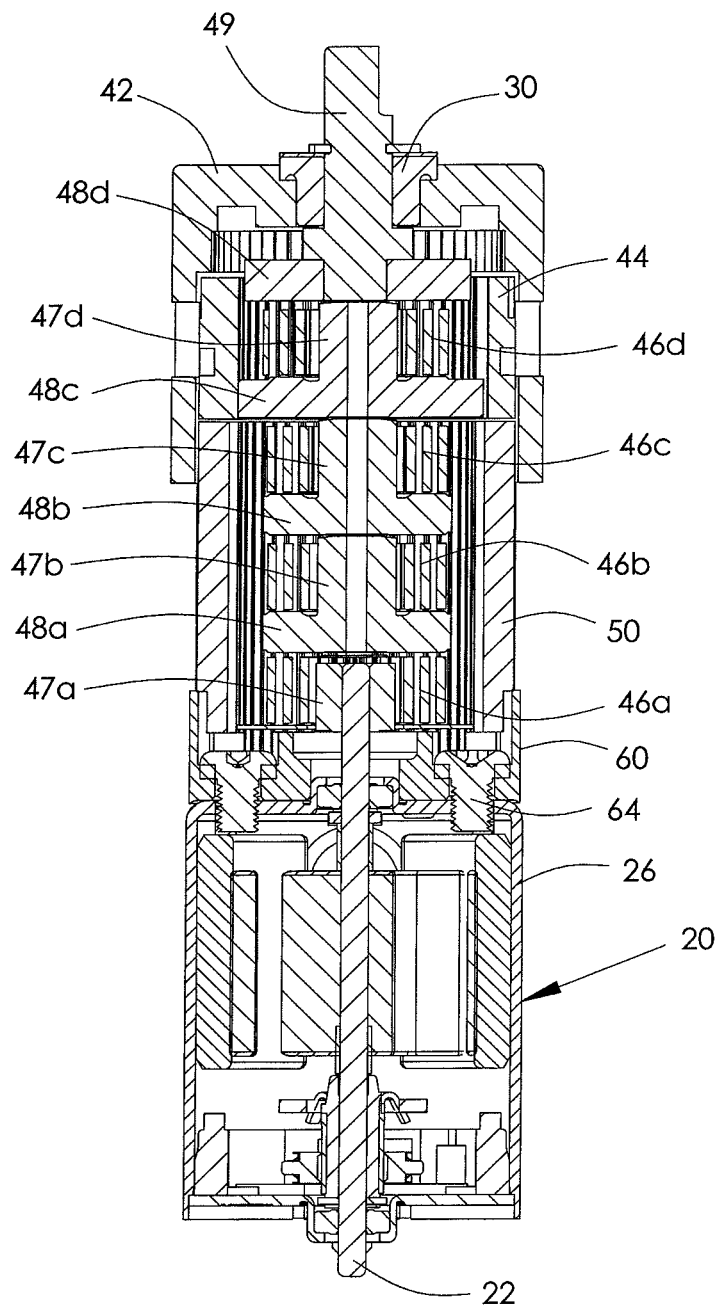
FIG. 4 is an enlarged sectional view of the motor assembly of FIG. 1.

FIG. 1 illustrates a motor assembly for a medical equipment in accordance with a preferred embodiment of the present invention. The medical equipment may be a surgical power tool which is manually switchable between drilling and screwing functions.

The motor assembly 10 has an output shaft 49 and comprises a motor 20 driving the output shaft through a gear train 40. FIG. 4 is a sectional view of the motor assembly and FIGS. 2 & 3 are partial views of the gear train.

Preferably, the motor 20 is a permanent magnet direct current motor which is powered by a battery. The motor 20 comprises a motor shaft 22 extending into the gear train 40. A pinion is fixed to the end of the motor shaft and forms the first sun gear 47a of the gear train.

As shown in FIGS. 2 to 4, the gear train 40 comprises a cylindrical cover 42, a movable ring gear 44 installed inside of the cover 42, and a multi-stage planetary gear set. The cover 42 is stationary relative to the stator or housing of the motor 20.

In this embodiment, the gear train 40 comprises a four-stage planetary gear set. Each stage comprises four planet gears 46a~46d, a sun gear 47a~47d meshed with the planet gears 46a~46d, and a carrier 48a~48d configured to support the planet gears 46a~46d on one side thereof. The sun gear 47a of the first stage planetary gear set is fixed to the motor shaft 22. The other sun gears 47b~47d are carried on the other side of the carrier 48a~48c of the preceding stage. The carrier 48d of the fourth and last stage is fixed with the output shaft 49. The third stage carrier 48c has outer teeth at the periphery thereof. The movable ring gear 44 has inner teeth 422 configured to mesh with the outer teeth of the carrier 48c and the planet gears 46d of the fourth stage.

The gear train 40 further comprises a fixed ring gear 50 which is fixed relative to the stator or housing of the motor 20. The fixed ring gear has internal teeth which are in mesh with the planet gears 46a~46c of the first, second and third stages. Carriers 48a~48b, which are nearer to the motor 20 than the carrier 48c, are disposed inside the fixed ring gear 50. Carriers 48a~48b are not directly connected to the fixed ring gear and can rotate relative to the fixed ring gear.

The cover 42 has inner teeth 422 at the inner circumferential surface thereof. The movable ring gear 44 also has outer teeth 442. The movable ring gear is movable axially within the cover between a first position in which the outer teeth of the movable ring gear are engaged with the inner teeth of the cover and a second position in which the outer teeth of the movable ring gear are disengaged from the inner teeth of the cover. When the outer teeth 442 are engaged with the inner teeth 422 of the cover 42, the movable ring gear 44 is locked to and non rotatable relative to the cover 42. When the outer teeth 442 are disengaged from the inner teeth 422 of the cover, the movable ring gear is able to rotate freely within the cover. In both positions, the movable ring gear remains in mesh with the fourth stage planet gears 46d. The movable ring gear 44 has a groove 444 in the outer surface thereof. The cover 42 has a through opening 424 (such as a hole, aperture slot, etc.) corresponding to the groove 444 to provide access for an operator/tool to the groove 444 from outside of the cover 42, so as to slide the movable ring gear axially within the cover, between the first and second positions.

When the movable ring gear 44 is in the first position where the outer teeth 442 of the movable ring gear 44 are engaged with the inner teeth 422 of the cover 42 and the movable ring gear 44 is not rotatable relative to the cover 42, the inner teeth of the movable ring gear 44 are only meshed with the planet gears 46d and do not meshed with the outer teeth of the carrier 48c. Each stage of the planetary gear set is working to reduce the rotational speed of the output shaft. Thus the gear reduction ratio of the gear train is high and the gear train 40 produces a low speed, high torque rotation of the output shaft 49.

When the movable ring gear 14 is in the second position where the outer teeth 442 of the movable ring gear 44 are disengaged from the inner teeth 422 of the cover 42 and the inner teeth of the movable ring gear 44 are meshed with the outer teeth of the carrier 48c and the planet gears 46d, the movable ring gear 44 is rotatable relative to the cover 42. The carrier 48c, sun gear 47d mounted on the carrier 48c, the planet gears 46d, the carrier 48d and the movable ring gear 44 are connected/combined together to become one unit which is rotatable relative to the cover 42. Thus, the fourth stage of the gear train acts as a direct connection and provides no speed reduction. Thus the gear train 40 has a lower gear reduction ratio and produces a higher speed and lower torque rotation of the output shaft 49.

In the present invention, the gear train 40 is able to provide an adjustable rotational speed of the output shaft by selectively moving the movable ring gear 44 between the first and second positions.

As the motor assembly is for use in medical equipment and in particular, as a motor assembly of a surgical tool, there is a desire for the motor assembly to be reliable and economical. Surgical equipment must be sterile and either able to be re-sterilized or disposable. This motor assemble can be made with parts of the gear train, including the cover, bracket, fixed ring gear and movable ring gear being made out of plastic material, especially by injection molding. Preferably, all parts of the gear train may be made from plastic materials One item which prevents the motor assembly from being re-sterilized is the grease on the gear train. By making components of the gear train out of plastic materials, the gear train can function satisfactory without added grease or oil for even complex surgeries and is inexpensive enough to be disposable. For reusable surgical tools, requiring sterilization, such as by an autoclave, solid lubricants and/or self lubricating plastic materials can be used for the gear train, including the output bearing 30. Indeed, the output bearing may be formed as an integral part of the cover or be formed by the cover as a monolithic molded part.

The cover 42 is preferably fixed to the fixed ring gear 50 by press fitting an end of the fixed ring gear into the open end of the cover. Bonding, such as by glue, may be used instead of or to strengthen the press fit connection. A tongue and groove connection between the fixed ring gear allows the connection to withstand the rotational forces which develop between the fixed ring gear and the cover during use of the tool.

The fixed ring gear is fixed to the motor housing 26 by a mounting bracket 60. The connection between the fixed ring gear 50 and the mounting bracket 60 also needs to withstand rotational forces which develop between the bracket and the fixed ring gear. The bracket has grooves (not shown) into which fingers 52 formed on an end of the fixed ring gear extend. These fingers and grooves prevent the fixed ring gear from rotating about the axis with respect to the bracket. The bracket as apertures 62 which mate with locking tabs 54 formed on the fixed ring gear, preferably on or near the fingers 52. This provides a snap lock connection allowing the fixed ring gear to be pressed into the bracket and held together by shoulders of the locking tabs engaging the wall of the apertures 62.

The planet gears are rotatably mounted to the corresponding carrier by spigots 45 which allow the planet gears to rotate while still driving the carriers. During assembly, the movable ring gear 44 is placed inside the cover 42 before the cover is mated with the fixed ring gear 50. The output shaft is fitted to carrier 48d having planet gears 46d mounted on spigots 45 and is fitted to the output bearing 30 on the cover 42. The planet gears 46d are meshed with the movable ring gear 44. Carrier 48c, with sun gear 47d and planet gears 46c is placed inside the cover with the sun gear 47d in mesh with the planet gears 46d and the planet gears 46c in mesh with the fixed ring gear. Carrier 48b, with sun gear 47c and planet gears 46b are placed inside the fixed ring gear with the sun gear 47c in mesh with the planet gears 46c and the planet gears 46b being in mesh with the fixed ring gear. Carrier 48a, with sun gear 47b and planet gears 46a is placed inside the fixed ring gear with the sun gear 47b in mesh with the planet gears 46b and the planet gears 46a in mesh with the fixed ring gear.

The mounting bracket 60 is fixed to the motor housing 26 by screws 64 or the like to fix the bracket to the motor 20. Sun gear 47a is fixed to the end of the motor shaft 22. As the fixed ring gear is pressed into the bracket so as to lock the fixed ring gear to the motor via the bracket, guided by the fingers on the fixed ring gear and the grooves in the bracket and locked there by the locking tabs 54 and apertures 62, the sun gear 47a is brought into mesh with the planet gears 46a and the assembly is complete. The motor has motor terminals 24 for connecting the motor to a source of power. As illustrated in FIG. 4, the motor is preferably a permanent magnet direct current motor, allowing the motor assembly to be powered from a battery, furthering its appeal as a disposable item and allowing the surgical tool to be fully self contained.

In the description and claims of the present application, each of the verbs "comprise", "include", "contain" and "have", and variations thereof, are used in an inclusive sense, to specify the presence of the stated item but not to exclude the presence of additional items.

Although the invention is described with reference to one or more preferred embodiments, it should be appreciated by those skilled in the art that various modifications are possible. Therefore, the scope of the invention is to be determined by reference to the claims that follow.

For example, the locking way to prevent the movable ring gear 44 from rotating relative to the cover 42 may be any other means. For example, recesses are formed on one of the inner surface of the cover 42 and outer surface of the ring gear 44 and protections are formed on the other of the inner surface of the cover 42 and the outer surface of the ring gear 44. When the projections are received in the recesses the ring gear 44 is prevented from rotating relative to the cover 42.

The invention claimed is:

1. A motor assembly of a surgical tool, comprising a motor having a motor shaft and a gear train driven by the motor,
   the gear train comprising: an output shaft; a fixed ring gear; a cover; a movable ring gear installed inside the cover; and a multi-stage planetary gear set, each stage comprising a sun gear, a carrier, and planet gears mounted on one side of the carrier and in mesh with the sun gear and one of the fixed ring gear and the movable ring gear,
   wherein the movable ring gear has inner teeth formed on an inner peripheral surface and one of the carriers has outer teeth formed on an outer peripheral surface;
   the movable ring gear is movable between a first position where the movable ring gear is engaged with an non-rotatable relative to the cover and is disengaged from said one carrier, whereby the gear train has a higher gear reduction ratio, and a second position where the movable ring gear is disengaged from the cover and is engaged with and rotatable with said one carrier and the planet gears adjacent to the other side of said one carrier whereby the gear train has a lower gear reduction ratio; and
   wherein the gear train includes a mounting bracket which is fixed to the motor and the fixed ring gear is fixed to the mounting bracket by a snap fit connection.

2. The motor assembly of claim 1, wherein the cover has a cylindrical configuration and has inner teeth on an inner surface thereof, and the movable ring gear has outer teeth configured to engage with the inner teeth of the cover when the movable ring gear is in the first position.

3. The motor assembly of claim 1, wherein the movable ring gear has a groove in an outer surface thereof, and the cover has a through opening to provide external access to the groove for moving the movable ring gear between the first and second positions.

4. The motor assembly of claim 1, wherein the gear train comprises a four-stage planetary gear set.

5. The motor assembly of claim 1, wherein the fixed ring gear is disposed nearer to the motor than the movable ring gear and the planet gears nearer to the motor than said one carrier are in mesh with the fixed ring gear.

6. The motor assembly of claim 1, wherein when the movable ring gear is located in the first position, the planet gears adjacent to said one carrier are in mesh with the inner teeth of the movable ring gear and are rotatable relative to the movable ring gear.

7. The motor assembly of claim 1, wherein the motor is a permanent magnet direct current motor.

8. The motor assembly of claim 1, wherein the fixed ring gear has fingers extending axially and engaging with the mounting bracket to prevent the fixed ring gear rotating with respect to the motor.

9. A surgical tool incorporating the motor assembly of claim 8.

10. The motor assembly of claim 1, wherein the fixed ring gear, movable ring gear, cover, and planet gears are made from plastics material.

11. A surgical tool incorporating the motor assembly of claim 10.

12. The motor assembly of claim 10, wherein the gear train is oil and grease free.

13. A surgical tool incorporating the motor assembly of claim 12.

14. A surgical tool, switchable between drilling and screwing functions, the surgical tool comprising the motor assembly of claim 1.

15. A motor assembly of a surgical tool, comprising a motor having a motor shaft and a gear train driven by the motor,
   the gear train comprising: an output shaft; a fixed ring gear; a cover; a movable ring gear installed inside the cover; and a multi-stage planetary gear set, each stage comprising a sun gear, a carrier, and planet gears mounted on one side of the carrier and in mesh with the sun gear and one of the fixed ring gear and the movable ring gear,
   wherein the movable ring gear has inner teeth formed on an inner peripheral surface and one of the carriers has outer teeth formed on an outer peripheral surface;
   the movable ring gear is movable between a first position where the movable ring gear is engaged with and non-rotatable relative to the cover and is disengaged from said one carrier, whereby the gear train has a higher gear reduction ratio, and a second position where the movable ring gear is disengaged from the cover and is engaged with and rotatable with said one carrier and the planet gears adjacent to the other side of said one carrier whereby the gear train has a lower gear reduction ratio; and
   wherein the fixed ring gear is a connected to the cover by a tongue and groove press fit.

16. A surgical tool incorporating the motor assembly of claim 15.

17. The motor assembly of claim 15, wherein the cover has a cylindrical configuration and has inner teeth on an inner surface thereof, and the movable ring gear has outer teeth configured to engage with the inner teeth of the cover when the movable ring gear is in the first position.

18. The motor assembly of claim 15, wherein the movable ring gear has a groove in an outer surface thereof, and the cover has a through opening to provide external access to the groove for moving the movable ring gear between the first and second positions.

19. The motor assembly of claim 15, wherein the fixed ring gear, movable ring gear, cover, and planet gears are made from plastics material.

20. The motor assembly of claim 15, wherein the gear train is oil and grease free.

* * * * *